United States Patent [19]

Hayman

[11] Patent Number: 4,968,605
[45] Date of Patent: * Nov. 6, 1990

[54] IMMOBILIZATION OF ENZYMES ON POROUS MELT SPUN POLYAMIDE YARNS

[75] Inventor: Nigel W. Hayman, Cheltenham, England

[73] Assignee: Imperial Chemical Industries plc, London, England

[ * ] Notice: The portion of the term of this patent subsequent to Apr. 18, 2006 has been disclaimed.

[21] Appl. No.: 136,353

[22] Filed: Dec. 22, 1987

[30] Foreign Application Priority Data

Jan. 27, 1987 [GB] United Kingdom ............... 8701706

[51] Int. Cl.$^5$ ..................... C12P 1/00; C12N 11/08; C12N 11/06
[52] U.S. Cl. ...................................... 435/41; 435/180; 435/181
[58] Field of Search ............. 435/41, 174, 177, 180, 435/181, 182

[56] References Cited

U.S. PATENT DOCUMENTS

| | | | |
|---|---|---|---|
| 4,345,414 | 8/1982 | Bornat et al. | 53/425 |
| 4,657,742 | 4/1987 | Beaver | 422/240 |
| 4,757,014 | 7/1988 | Hendrickson et al. | 435/180 |
| 4,822,678 | 4/1989 | Brody et al. | 428/36.4 |

FOREIGN PATENT DOCUMENTS

| | | |
|---|---|---|
| 0008498 | 3/1980 | European Pat. Off. . |
| 0080274 | 6/1983 | European Pat. Off. . |
| 0179603 | 4/1984 | European Pat. Off. . |
| 0186125 | 7/1986 | European Pat. Off. . |
| 0246752 | 11/1987 | European Pat. Off. . |
| 0272025 | 6/1988 | European Pat. Off. . |
| 0272026 | 6/1988 | European Pat. Off. . |
| 1309295 | 3/1973 | United Kingdom . |
| 1485123 | 9/1977 | United Kingdom . |
| 2018410 | 10/1979 | United Kingdom . |

OTHER PUBLICATIONS

Chemical Abstracts, vol. 93, No. 13, Sep. 29, 1980, p. 276, Abstract No. 127976y, Columbus, OH, US; B L Seng et al.
Patent Abstracts of Japan, vol. 8, No. 138 (C-231) (1575), Jun. 27, 1984, European Search Report of Mar. 29, 1988.
Process Biochemistry, Aug. 1972, Dinelli, "Fibre-Entrapped Enzymes", pp. 9–12.
Jr. of Molecular Catalysis, 2(1977), 453–458.
Jr. of Applied Polymer Science vol. 27, 1665–1674 (1982).
Jr. of Applied Polymer Science, vol. 28, 1447–1455 (1983).
Bulletin of Res Insv for Polymers & Textiles, No. 139, 65–70 (1984), Japan.
Analytical Chemistry, vol. 57, No. 2, Feb. 1985, 565–566.
Biotechnology and Bioengineering, vol. XXVII, pp. 1077–1080 (1985).
Biochimica et Biophysics Acta., 612 (1980), 305–316.
Febs Letters, vol. 81, No. 2, Sep. 1977, 326–330.
"A New method for the Production of Optically Active Aminoacids", Dinelli et al., Laboratori Processi Microbiologici, Rome, Italy, 477–481.

Primary Examiner—David M. Naff
Attorney, Agent, or Firm—Cushman, Darby & Cushman

[57] ABSTRACT

An immobilized enzyme structure in which molecules of one or more enzymes are attached to chemically active groups located on surface in the structure, such structure being composed of melt spun polyamide fibres comprising spaced fibrils of polyamide which are substantially aligned to the axis of the fibre, such aligned spaced fibrils being interconnected to each other in a random manner.

7 Claims, No Drawings

IMMOBILIZATION OF ENZYMES ON POROUS MELT SPUN POLYAMIDE YARNS

IMMOBILISATION OF ENZYMES

This invention relates to the immobilisation of enzymes on fibrous supports and the use of such immobilised enzymes in an enzyme catalysed reaction.

Enzymes are proteins which catalyse chemical reactions. However their utility for various applications has been limited since it is difficult to separate enzymes from reaction media, thus limiting product purity. Moreover soluble enzymes may generally be used only once in a batch reaction and, because of the high costs of many enzymes, their industrial use has been limited, even though they are extremely efficient catalysts.

For many years much research effort has been devoted to devising techniques for immobilising enzymes by attaching or bonding them to water-insoluble carrier materials in such a way that the enzymes are rendered immobile yet remain catalytically active. However, known immobilised enzyme support structures have several disadvantages, for example some, in use, exhibit unsatisfactory flow properties or low enzyme activity yields or low enzyme binding or decreased stability. Thus an increasing need exists to develop improved immobilised enzyme support structures.

Various attempts have been made to immobilise enzymes by confining the enzyme within a fibrous support made from a variety of fibrous polymeric materials. Fibres can be used in many forms including chopped fibres, tow, long filaments, yarns, fabrics which may be woven, knitted or non-woven and in composites. In addition, porous fibres can be made with high specific surface areas which enhances conversion rates. In those cases where diffusion into the fibrous structure is required, the small diameters possible with fibres can essentially eliminate diffusion as a rate-controlling factor. Fibrous supports, which are ideally chemically inert can be prepared with good mechanical strength and durability, and they can usually be easily separated from the reaction medium.

One of the first studies of the use of fibrous immobilised enzymes was that of Dinelli who wet-spun solutions of polymers mixed with enzymes. Process Biochem. 7(8), 9-15(1972). The polymers included cellulose diacetate, cellulose triacetate, ethyl cellulose, nylon, polyvinyl chloride and α-methylpolyglutamate. The enzymes included invertase, β-galactosidase, glucose oxidase, hexokinase, phosphohexose-isomerase, fructose-phosphate kinase and aldolase.

Grazi et al. produced cellulose triacetate fibres with sucrose phosphorylase embedded in them following the procedure of Dinelli. J Mol Catal 2(6), 453-458 (1977).

Ichijo et al immobilised invertase by adsorption on very fine polyvinyl alcohol fibres which had been aminated. The authors postulated that the invertase was bound to the animated fibres by ionic forces. J Appl Polym Sci 27, 1665-1674 (1982).

Ichijo published an additional paper on the use of these aminated fibres for immobilising invertase. J Appl Polym Sci 28 1447-1455 (1983). He summarised the advantages for immobilising enzymes in this way as follows:

(1) Functional groups can easily be incorporated into the fibres,
(2) The fibres adsorb a large amount of enzyme because of their porosity and large surface area,
(3) The fibres can be formed into a variety of shapes suitable for many kinds of enzyme reactions
(4) The experimental procedure for immobilisation is simple because the enzymes are immobilised by ionic bonds.

Ichijo prepared a nonwoven fabric or filter paper from his aminated polyvinyl alcohol fibres containing adsorbed invertase. Bulletin of Res Inst for Polymers and Textiles, Japan, No 139, 65-70 (1984). He made an enzyme reactor by inserting the filter paper in a holder and passing a sucrose solution continuously through the filter paper. The immobilised enzyme showed high activity in producing glucose, but the flow resistance of the filter paper increased with increased sucrose concentration.

He later made knitted fabrics from his polyvinyl alcohol fibres with adsorbed invertase and passed a sucrose solution along a thin channel parallel to and in contact with the knitted fabric in a reactor. Biotechnol Bioeng 27, 1077-1080 (1985). The reactor was successfully operated for converting sucrose to glucose.

EP 8498A relates to the immobilisation of enzymes on modified nylon particles.

Arnold developed a novel enzyme-based fibre optic sensor by immobilising alkaline phosphatase at the surface of nylon fibres by covalent bonding. Anal Chem 57, 565-566 (1985).

A number of other references disclose the immobilisation of enzymes using nylon fibres including Bisse et al.—(1977) FEBS Letts 81, 326-330; Carvajal et al.—(1978) Biochem Biophys Acta 612, 305-316; Dinelli et al.—Enzyme Engineering Vol 3, p 477-481 Ed by Pye EK and Weetall H H, Plenum Press, New York.

Also with the advent of hollow fibres, considerable work has also been conducted in immobilising enzymes in these structures.

In our copending UK patent application No 8611974 we have described a novel melt spun fibre having two polymeric fibrous components and containing from 30 to 70 parts by weight of a first component and from 70 to 30 parts by weight of a second component, each component being present in the fibre as fibrils which are substantially aligned to the axis of the fibre, such aligned fibrils being interconnected to each other in a random manner, such interconnections penetrating through the fibrils of the other component such that both components exist in the fibre as interpenetrating networks.

A feature of such fibres is that either of the components can be leached out using a suitable solvent so producing a high surface area porous fibre of the other component. Furthermore, if the first component is nylon, then after the second component, for example polypropylene, has been leached out, the porous yarn so formed contains nylon ends with active amine groups, to which enzymes can be attached through conventional linking agents and retained within the cavities within the porous fibre.

Therefore, according to the present invention we provide an immobilised enzyme structure in which molecules of one or more enzymes are attached to chemically active groups located on the surfaces in the structure, such structure being composed of melt spun polyamide fibres comprising spaced fibrils of polyamide which are substantially aligned to the axis of the fibre, such aligned spaced fibrils being interconnected to each other in a random manner.

Also according to the invention we provide a process for performing an enzyme—catalysed reaction wherein the enzyme is in the form of an immobilised enzyme structure in which molecules of one or more enzymes are covalently linked to chemically active groups which are located on surfaces in the structure, such structure being composed of melt spun porous polyamide fibres comprising spaced fibrils of polyamide which are substantially aligned to the axis of the fibre, such aligned spaced fibrils being interconnected to each other in a random manner.

A wide variety of enzymes can be immobilised on such fibrous structures using conventional linking agents, which can link functional groups in the enzyme to free amine ends on the polyamide, such as glutaraldehyde and bifunctional diimidates such as dimethyl pimelimidate. This may be achieved by adding the linking agent to provide an activated structure and then adding the enzyme in solution. The enzyme attaches itself to the linking agent through covalent bonding and is retained within the porous fibre structure.

The density of the enzyme loading which can be achieved on the structure depends on the density of the active ends on the structure and their availability, through the openness of the pores, for linkage with any particular enzyme. On the other hand we have found that at higher enzyme loadings, the activity of the immobilised enzymes in catalysing bio-reactions decreases and in the immobilised structure, we prefer that between 10% and 50% of the active ends are connected to molecules of the enzyme.

Preferred enzymes for immobilisation are the smaller enzymes having molecular weights up to 200000 including D-2-monochloropropionate dehalogenase, as described in EP 179603A horse-radish peroxidase and amidase, the latter being referred to in our copending UK Patent Applications Nos 8630029 and 8630012. Nevertheless larger enzymes having higher molecular weights can be immobilised on the described structures.

We prefer that the invention is applied to purified enzymes is enzymes extracted from microbial cells but the invention is not limited to purified enzymes and can be applied to enzymes contained in whole cells.

The fibrous structure used in the invention provides a cheap, chemically inert, support to which one or more different enzymes may be covalently linked so providing a stronger attachment which stabilises the enzymes. Enzymes immobilised in this fibrous structure can be re-used.

The fibrous structure may be in the form of individual fibres or alternatively may be a woven or knitted fabric produced from such fibres.

Enzymes immobilised in the manner of the invention can be used in many types of bioreactors. The enzymes can be immobilised on the surfaces in a fabric mesh through which the liquid to be treated flows or alternatively the enzymes can be immobilised in small pieces of material which can be stirred around in the reaction liquid. As mentioned previously, two or more different enzymes can be immobilised at the same time on the same fibrous structure.

The present invention will now be described with reference to the following Example:

EXAMPLE 560 grams of dried nylon 6.6 having a relative viscosity of 40, and which has approximately 45 amine end groups, was chip blended with 40 grams of dried nylon 11 (a compatibiliser) and 400 grams of polypropylene (MF1 25) and then spun at 290° C. using a small screw extruder, through a 60 grade alumina filter and a 5×9 thou hole spinneret. The yarn so formed was wound up at 500 meters/minute, a spin finish was applied and 130 f5 yarn produced. This was drawn, with a 85° C. feed roll, at 100 meters/minute to produce 39 f 5 yarn.

The nylon 66 and polypropylene is present in the fibrous yarn as fibrils which are substantially aligned to the axis of the fibre, such aligned fibrils being interconnected to each other in a random manner, such interconnections in one of the components penetrating through the fibrils of the other component such that both components exist in the fibre as interpenetrating networks.

The yarn was subsequently knitted into a fabric panel which was boiled in p-xylene for three hours in order to extract a substantial proportion of the polypropylene present in the fibres in the fabric. The fibres in the fabric then had a porous structure comprising spaced fibrils of nylon 66 which are substantially aligned to the axis of the fibre, such aligned spaced fibrils being interconnected to each other in a random manner.

Fabric (No 2353) was cut into squares of approximately 1 cm$^2$. These was dried in a vacuum oven at 75° C. overnight to remove residual p-xylene, washed in aqueous quadralene, deionised water and then stored in 50 mM potassium phosphate buffer pH 7.0.

Individual squares of cloth (10.8 mg) were placed in 1 ml of 0.05% aqueous gluteraldehyde for 2 hours at room temperature and were then washed with 20 mM ethanolamine buffer pH 7.5 containing 0.1 mg/ml diphiothreitol.

D-2-chloropropionate dehalogenase solutions of specific activity 14 U/mg protein and activity 10.2 U/ml in 20 mM ethanolamine buffer pH 7.5 containing 0.1 mg/ml diphiothreitol were used for immobilisation.

1 unit (U) of enzyme activity catalyses the conversion of 1$\mu$ mole D-2-chloropropionate (to L-lactate plus chloride) in 1 minute at 30° C. and at pH 7.5.

Each piece of gluteraldehyde activated cloth was placed in 0.5 ml of enzyme solution and left at 4° C. for 48 hours with gentle agitation.

Pieces of fabric treated in this way and washed with 20 mM ethanolamine buffer pH 7.5 were tested for the ability to dehalogenate D-2-chloropropionate in a standard assay. An activity of 0.04 mM Cl released/minute/piece cloth was recorded in this assay. Comparison of this activity with that lost from the original enzyme sample showed a 95% recovery of activity.

Standard assay 1 piece of cloth with immobilised enzyme was incubated with agitation at 30° C. in a mixture of 1.5 ml of 1M potassium phosphate pH 7.5 and 0.5 ml of 1M sodium chloropropionate pH 7.0.

Chloride release over a several hour period was measured by injecting 100 $\mu$l samples from this assay mixture into a 'Marius chlor-o-counter'.

I claim:

1. An immobilised enzyme structure in which molecules of one or more enzymes are attached to free amine ends located on the surfaces of porous melt spun polyamide yarns comprising spaced fibrils of polyamide which are substantially aligned to the axis of the yarn, such aligned spaced fibrils being interconnected to each other in a random manner.

2. An immobilised enzyme structure as claimed in claim 1 in which the enzymes are attached to the yarns by means of an agent which links the functional groups in the enzyme to the free amine ends on the fibrils.

3. An immobilised enzyme structure as claimed in claim 2 in which the agent is either glutaraldehyde or a bifunctional diimidate.

4. An immobilised enzyme structure as claimed in claim 2 in which between 10% and 50% of the free amine ends in the polyamide yarns are attached to the enzyme molecules.

5. An immobilised enzyme structure as claimed in any one of the preceding claims in which the enzyme has a molecule weight up to 200000.

6. An immobilised enzyme structure as claimed in claim 5 in which the enzyme is selected from D-2-monochloropropionate dehalogenase, horse-radish peroxidase or amidase.

7. A process for performing an enzyme-catalysed reaction wherein the enzyme is in the form of an immobilized enzyme structure in which molecules of one or more enzymes are covalently linked to free amine ends which are located on the surfaces of melt spun porous polyamide yarns comprising spaced fibrils of polyamide which are substantially aligned to the axis of the yarn, such aligned spaced fibrils being interconnected to each other in a random manner.

* * * * *